(12) United States Patent
Li et al.

(10) Patent No.: US 7,939,343 B2
(45) Date of Patent: May 10, 2011

(54) METHOD FOR DETECTING AN UNKNOWN CONTAMINANT CONCENTRATION IN A SUBSTANCE

(75) Inventors: Yanbin Li, Fayetteville, AR (US); Xiao-Li Su, Fayetteville, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 348 days.

(21) Appl. No.: 11/860,180

(22) Filed: Sep. 24, 2007

(65) Prior Publication Data

US 2008/0206791 A1 Aug. 28, 2008

Related U.S. Application Data

(63) Continuation of application No. 11/329,009, filed on Jan. 9, 2006, now abandoned.

(60) Provisional application No. 60/642,335, filed on Jan. 7, 2005.

(51) Int. Cl.
*G01N 33/543* (2006.01)
*G01N 13/00* (2006.01)

(52) U.S. Cl. .......................................... 436/518; 73/579

(58) Field of Classification Search .................. None
See application file for complete search history.

(56) References Cited

U.S. PATENT DOCUMENTS

| | | | |
|---|---|---|---|
| 4,849,232 A | 7/1989 | Baker et al. |
| 4,946,651 A | 8/1990 | Liston et al. |
| 5,135,852 A | 8/1992 | Ebersole et al. |
| 5,518,895 A | 5/1996 | Thorpe et al. |
| 5,856,175 A | 1/1999 | Thorpe et al. |
| 5,892,144 A | 4/1999 | Meller et al. |
| 6,033,574 A | 3/2000 | Siddiqi |
| 6,300,123 B1 | 10/2001 | Vadgama et al. |
| 6,300,141 B1 | 10/2001 | Segal et al. |
| 6,326,144 B1 | 12/2001 | Bawendi et al. |
| 6,326,563 B1 | 12/2001 | Takeuchi et al. |
| 6,386,053 B1 | 5/2002 | Takeuchi et al. |
| 6,468,808 B1 | 10/2002 | Nie et al. |
| 6,506,381 B1 | 1/2003 | Bitensky et al. |
| 6,623,982 B1 | 9/2003 | Liberti et al. |
| 6,645,731 B2 | 11/2003 | Terstappen et al. |
| 7,081,489 B2 | 7/2006 | Chen et al. |
| 2002/0098529 A1 | 7/2002 | Tan et al. |
| 2003/0095656 A1 | 5/2003 | Sommer |
| 2003/0170613 A1 | 9/2003 | Straus |
| 2004/0067503 A1 | 4/2004 | Tan et al. |
| 2004/0126279 A1 | 7/2004 | Renzi et al. |
| 2004/0137430 A1 | 7/2004 | Anderson et al. |
| 2004/0157271 A1 | 8/2004 | Kirakossian et al. |
| 2004/0191886 A1 | 9/2004 | Wertz et al. |
| 2004/0197899 A1 | 10/2004 | Gomez et al. |
| 2005/0059105 A1 | 3/2005 | Alocilja et al. |
| 2005/0074904 A1 | 4/2005 | Chin et al. |
| 2005/0106064 A1 | 5/2005 | Laurell et al. |
| 2006/0063149 A1 | 3/2006 | Berthet et al. |
| 2006/0112438 A1 | 5/2006 | West et al. |
| 2006/0127360 A1 | 6/2006 | Berinstein et al. |
| 2006/0217893 A1 | 9/2006 | Li et al. |
| 2007/0114181 A1 | 5/2007 | Li et al. |
| 2008/0135490 A1 | 6/2008 | Li et al. |

FOREIGN PATENT DOCUMENTS

WO WO 2008/028124 3/2008

OTHER PUBLICATIONS

Aizawa et al., "Conventional detection method of fibrinogen and fibrin degradation products using latex piezoelectric immunoassay," Biosensors and Bioelectronics, vol. 18 (2003) 765-771.*
Amagliani, G., et al., "Direct detection of *Listeria monocytogenes* from milk by magnetic based DNA isolation and PCR." Food Microbiol. 21(5):597-603 (2004).
Ball, H. J., et al. "The detection of verocytotoxins in bacterial cultures from human diarrheal samples with monoclonal antibody-based Elisas." J. Med. Microbiol. 44(4):273-276 (Apr. 1996).
Bennett, A. R., et al., "The isolation and detection of *Escherichia coli* O157 by use of immunomagnetic separation and immunoassay procedures." Lett. Appl. Microbiol. 22(3):237-243 (Mar. 1996).
Bruchez Jr., M, et al., "Semiconductor nanocrystals as fluorescent biological labels." Science 281(5385):2013-2016 (Sep. 25, 1998).
Captivate™ ferrofluid conjugates and related products, MP 21473. Rev: Dec. 3, 2001. Molecular Probes, Eugene, OR, USA.
Centers for Disease Control and Prevention (CDC). "Disease Information—*E. coli* O157:H7." website (www.cdc.gov) (2004).
Chan, W. C., et al., "Quantum dot bioconjugates for ultrasensitive nonisotopic detection." Science 281(5385):2016-2018 (Sep. 25, 1998).
Chapman, P.A. et al., "Use of commercial enzyme immunoassays and immunomagnetic separation systems for detecting *Escherichia coli* O157 in bovine fecal samples." Applied and Environmental Microbiology 63(7):2549-2553 (Jul. 1997).
Che, Y. H., et al., "Rapid detection of *Salmonella* Typhimurium in chicken carcass wash water using an immunoelectrochemical method." J. Food Protect. 63(8):1043-1048 (Aug. 2000).
Che, Y. H., et al., "Rapid detection of *Salmonella* Typhimurium using an immunoelectrochemical method coupled with immunomagnetic separation." J. Rapid Methods Automat. Microbiol. 7:47-59 (1999).
Cloak, O. M., et al., "Development of a surface adhesion immunofluorescent technique for rapid detection of *Salmonella* spp. from meat and poultry." J. Appl. Microbiol. 86(4):583-590 (Apr. 1999).
Deisingh, A. K., et al., "Strategies for the detection of *Escherichia coli* O157:H7 in foods." J. Appl. Microbiol. 96(3):419-429 (2004).

(Continued)

*Primary Examiner* — Marjorie Moran
*Assistant Examiner* — Anna Skibinsky
(74) *Attorney, Agent, or Firm* — Michael Best & Friedrich LLP

(57) ABSTRACT

A method for determining a concentration of a contaminant in a first sample, the method including producing the first sample, including adding a plurality of immuno-beads to a test substance; exposing a crystal microbalance immunosensor to the first sample; determining a change in a first motional resistance of the crystal microbalance immunosensor following exposure to the first sample ($\Delta R_1$); and determining the concentration of the contaminant in the first sample according to $\Delta R_1$.

20 Claims, 14 Drawing Sheets

OTHER PUBLICATIONS

Dubertret, B., et al., "In vivo imaging of quantum dots enscapsulated in phospholipid micelles." Science 298(5599):1759-1762 (Nov. 29, 2002).

Fratamico, P. M., et al., "Rapid isolation of *Escherichia coli* O157:H7 from enrichment cultures of foods using an immunomagnetic separation method." Food Microbiol. 9(2):105-111 (1992).

Fritzsche, W., et al., "Metal nanoparticles as labels for heterogeneous, chip-based DNA detection." Nanotechnology 14:R63-R73 (2003).

Gehring, A.G. et al., "Use of a light-addressable potentiometric sensor for the detection of *Escherichia coli* O157:H7." Anal Biochem 258(2):293-298 (May 1, 1998).

Gehring, A. G., et al., "Enzyme-linked immunomagnetic electrochemical detection of *Salmonella* Typhimurium." J. Immunol. Methods 195(1-2):15-25 (Sep. 9, 1996).

Gu, H., et al. "Using biofunctional magnetic nanoparticles to capture Gram-negative bacteria at an ultra-low concentration." Chemical Communications (Cambridge, United Kingdom) 15:1966-1967 (Aug. 7, 2003).

Gu, H., et al., "Biofunctional magnetic nanoparticles for pathogen detection." 226th ACS National Meeting, NY. ACS, Washington DC, USA (2003).

Hage, D. S. "Immunoassays." Anal. Chem. 71:294R-304R (1991).

Jaiswal, J. K., et al., "Long-term multiple color imaging of live cells using quantum dot bioconjugates." Nat. Biotechnol. 21(1):47-51 (Jan. 2003).

Karch, H., "Isolation of Enterohemorrhagic *Escherichia coli* O157 Strains from Patients with Hemolytic-Uremic Syndrome by Using Immunomagnetic Separation, DNA-Based Methods, and Direct Culture" Journal of Clinical Microbiology 34(3):516-519 (Mar. 1996).

Kemshead, J. T., et al., "A model system for the enrichment of tumor cells from peripheral blood and bone marrow using immuno-magnetic ferrofluids" p. 593-600. Advances in bone marrow purging and processing. Fourth International Symposium on Bone Marrow Purging and Processing. Orlando, Florida, USA (1993).

Kemshead, J.T. et al., "Immunomagnetic Colloids for the Enrichment of Tumor Cells from Peripheral Blood and Bone Marrow: A Model System" Journal of Hematotherapy 3(1):51-57 (Spring 1994).

Kim, S.K. et al., "Fabrication of comb interdigitated electrodes array (IDA) for a microbead-based electrochemical assay system," Biosens. Bioelectron. (2004) 20:887-894.

Larson, D.R., et al., "Water-soluble quantum dots for multiphoton fluorescence imaging in vivo." Science 300(5624):1434-1436 (May 30, 2003).

Lekowska-Kochaniak, A., D. et al., "Detection of *Escherichia coli* O157:H7 in raw meat by immunomagnetic separation and multiplex PCR." Acta Microbiol. Pol. 51(4):327-337 (2002).

Li, J., et al., "Piezoelectric immunosensor based on the magnetic nanoparticles with simple immobilization procedures." Anal. Chemica Acta 481:191-198 (2003).

Liberti, P. A., et al, "Bioreceptor ferrofluids: novel characteristics and their utility in medical applications.", p. 777-790. In E. Pelizzetti (ed.), Fine Particles Science and Technology. Kluwer Academic Publishers, Netherlands (1996).

Liu, R. H., et al., "Accoustic microstreaming for biological sample mixing enhancement." p. 545-550. 2nd Annual International IEEE-EMBS Special Topic Conference on Microtechnologies in Medicine & Biology. Madison, WI, USA (May 2-4, 2002), Poster 183.

Liu, Y., et al., "Rapid detection of *E. coli* O157:H7 inoculated in ground beef, chicken carcass, and lettuce samples with an immunomagnetic chemiluminescence fiber-optic biosensor." J. Food Prot. 66(3):512-517 (Mar. 2003).

Mansfield, L.P., et al., "The detection of *Salmonella* using a combined immunomagnetic separation and Elisa end-detection procedure." Lett. Appl. Microbiol. 31(4):279-283 (May 30, 2003).

Oleschuk, R. D., et al., "Trapping of bead-based reagents within microfluidic systems: On-chip solid-phase extraction and electrochromatography." Anal. Chem. 72(3):585-590 (Feb. 1, 2000).

Olsvik, O., et al., "Magnetic separation techniques in Diagnostic Microbiology." Clin. Microbiol. Rev. 7(1):43-54 (Jan. 1994).

Owen, C. S., "Magnetic sorting of leukocytes." Cell Biophy. 8(4):287-296 (Aug. 1986).

Parmar, N., et al., "The detection of *Salmonella enteritidis* and *Salmonella* Typhimurium using immunomagnetic separation and conductance microbiology." Lett. Appl. Microbiol. 15:175-178 (1992).

Peng, T., et al., "Amperometric detection of *Eschericia coli* heat-labile enterotoxin by redox diacetylenic vesicles on a sol-gel thin-film electrode." Anal. Chem. 72(7):1611-1617 (Apr. 1, 2000).

Peng, Z.G. et al. "Conformational Change of Adsorbed and Desorbed Bovine Serum Albumin on Nano-sized Magnetic Particles" Colloids and Surfaces B: Biointerfaces 33:15-21 (2004).

Perez, F.G. et al. "Immunomagnetic Separation with Mediated Flow Injection Analysis Amperometric Detection of Viable *Escherichia coli* O157" Anal. Chem. 70(11):2380-2386 (Jun. 1, 1998).

Pyle, B. H., et al., "Sensitive detection of *E. coli* O157 in food and water by immunomagnetic separation and solid-phase laser cytometry." Appl. Environ. Microbiol. 65(5):1966-1972 (May 1999).

Rosenthal, S. J., et al., "Targeting cell surface receptors with ligand-conjugated nanocrystals." J. Am. Chem. Soc. 124(17):4586-4594 (May 1, 2002).

Ruan, C., et al. "A Biensyme Electrochemical Biosensor Coupled with Immunomagnetic Separation for Rapid Detection of *Escherichia coli* O157:H7 in Food Samples" Transactions of the ASAE 45(1):249-255 (2002).

Sathaye, A., et al., "An acoustic vortex generation for microfluidic particle entrapment." p. 641-644, vol. 1. IEEE Ultrasonics Symposium. Atlanta, Georgia, USA (2001).

Seo K. H., et al., "Immunomagnetic separation and flow cytometry for raipd detection of *Escherichia coli* O157:H7." Journal of Food Protection. 61(7):812-816 (Jul. 1998).

Seong, G. H., et al., "Efficient mixing and reactions within microfluidic channels using microbead-supported catalysts." J. Am. Chem. Soc. 124(45):13360-13361 (Nov. 13, 2002).

Shaw, S. T., et al., "Performance of the Dynabeads anti-*Samonella* system in the detection of *Salmonella* species in foods, animal feeds, and environmental samples." J. Food Protect. 61(11):1507-1510 (Nov. 1998).

Soukka, T., et al., "Utilization of kinetically enhanced monovalent binding affinity by immunoassays based on multivalent nanoparticles-antibody bioconjugation." Anal. Chem. 73(14):2254-2260 (Jul. 15, 2001).

Stoimenov, P. K., et al., "Metal oxide nanoparticles as bactericidal agents." Langmuir 18:6679-6686 (2002).

Su, X., et al., "Quantum dot biolabeling coupled with immunomagnetic separation for detection of *Escherichia coli* O157:H7" Analytical Chemistry 76(16):4806-4810 (Aug. 15, 2004).

Sun, W., et al., "Comparison of ATP and in vivo Bioluminescence for Assessing the Efficiency of Immunomagnetic Sorbents for Live *Escherichia coli* O157:H7 Cells" Journal of Applied Microbiology 92(6):1021-1027 (2002).

Tan, W., et al., "Bionanotechnology based on silica nanoparticles." Med. Res. Rev. 24(5):621-638 (Sep. 2004).

Tibbe, A. G. J., et al., "Cell analysis system based on compact disk technology." Cytometry 47(3):173-182 (Mar. 1, 2002).

Tibbe, A. G. J., et al., "Magnetic field design for selecting and aligning immunomagnetic labeled cells." Cytometry 47(3):163-172 (Mar. 1, 2002).

Tibbe, A. G. J., et al., "Optical tracking and detection of immunomagnetically selected and aligned cells." Nat. Biotechnol. 17(12):1210-1213 (Dec. 1999).

Varshney, M., et al., "Magnetic Nanoparticle-Antibody Conjugates for the Separation of *Escherichia coli* o157:H7 in Ground Beef" J Food Protection 68(9):1804-1811 (Sep. 2005).

Varshney, M., et al., "Magnetic Immuno-nanoparticles for highly efficient separation of *Escherichia coli* O157:H7 from food samples." A poster presented at the Arkansas Section of ASAE 2004 Annual Meeting, Little Rock, AR (Oct. 1, 2004).

Varshney, M., et al., "A chemiluminescence biosensor coupled with immunomagnetic separation for rapid detection of *Salmonella* Typhimurium." J. Rapid Meth. Automat. Micobiol. 11:111-131 (2003).

Varshney, M., et al., "Magnetic immuno-nanoparticles for hightly efficient separation of *Escherichia coli* O157:H7 from food samples." A poster presented at the Food Safety Consortium 2004 Annual Meeting, October 3-5, Ames, IA. Abstract of the poster in: CD of Food Safety Consortium 2004 Annual Meeting—Agenda, Presentations, and Progress Reports.

Wang, H., et al., "PCR based fluorescent method for rapid detection of *Salmonella* Typhimurium in poultry samples." J. Rapid Meths. Auto. Microbiol. 10:83-92 (2002).

Watson, A., et al., "Lighting up cells with quantum dots" Biotech. 34(2):296-303 (Feb., 2003).

Wu, X., et al., "Immunofluorescent labeling of cancer marker Her2 and other cellular target with semiconductor quantum dots." Nat. Biotechnol. 21(1):41-46 (Jan. 2003).

Xu, J. et al., "Detection of avian influenza virus using an interferometric biosensor," Anal. Bioanal. Chem. (2007) 389:1193-1199.

Yang, L., et al., "Interdigitated array microelectrode-based electrochemical impedance immunosensor for detection of *Escherichia coli* O157:117." Anal. Chem. 76(4):1107-1113 (Feb. 15, 2004).

Yang, L., et al., "Rapid detection of *Salmonella* Typhimurium in food samples using a bienzyme electrochemical biosensor with flow injection." J. Rapid Methods Automat. Microbiol. 9:229-240 (2001).

Ye, J., "A Chemiluminescence Fiber-optic Biosensor Coupled with Immunomagnetic Separation for Rapid Detection of *E. Coli* O157:H7" Transactions of the ASAE 45(2):473-478 (2002).

Yu, H., et al., "Immunomagnetic-electrochemiluminescent Detection of *Escherichia coli* O157 and *Salmonella typhimurium* in Foods and Environmental Water Samples" Applied and Environmental Microbiology 62(2):587-592 (Feb. 1996).

Yu, L.S.L., et al., "Immunomagnetic Separation Methods for the Isolation of *Campylobacter jejuni* from Ground Poultry Meats" Journal of Immunological Methods 256(1-2):11-18 (Oct. 1, 2001).

Zhao, X., et al., "A Rapid Bioassay For Single Bacterial Cell Quantitation Using Bioconjugated Nanoparticles" PNAS 101(42):15027-15032 (Oct. 19, 2004).

Zhu, L., et al., "Quantum dots as a novel immunofluoresecent detection system for *Cryptosporidium parvum* and *Giardia lamblia*." Appl. Environ. Microbiol. 7(1)0:597-598 (Jan. 2004).

International Search Report and Written Opinion of Application No. PCT/US07/77376 dated Jan. 24, 2008 (14 pages).

United States Patent Office Action for U.S. Appl. No. 11/328020 dated Nov. 13, 2008 (11 pages).

United States Patent Office Action for U.S. Appl. No. 11/328808 dated Dec. 2, 2008 (9 pages).

Babacan, S. et al. "Piezoelectric flow injection analysis biosensor for the detection of *Salmonella typhimurium*." J. Food Sci. 67(1):314-320 (2002).

Brucker, G.A., "The quartz crystal microbalance, a versitile characterization tool for thin film coatings," Vacuum Technology & Coating (2005) 63-67.

Buttry, D.A., et al., "Measurement of interfacial process at electrode surfaces with the electrochemical quartz crystal microbalance." Chem. Rev. 92(6):1355-1379 (1992).

Cudjoe, K.S. et al., "Detection of Salmonella from raw food samples using Dynabeads® anti-Salmonella and a conventional reference method," Int. J. Food Microbiol. (1997) 37(1):55-62.

Deisingh, A.K. et al., "Detection of infectious and toxigenic bacteria," Analyst (2002) 127:567-581.

Dynal Biotech, "Dynabeads® anti-Salmonella" product description (2005) 2 pages.

Fredricksson, C., et al., "The piezoelectric quartz crystal mass and dissipation sensor: A means of studying cell adhesion." Langmuir 14:248-251 (1998).

Fung, Y.S., et al., "Self-assembled monolayers as the coating in a quartz piezoelectric crystal immunosensor to detect *Salmonella* in aqueous solution." Anal. Chem. 73:5302-5309 (2001).

Holt, J.G., et al., "Bergey's Manual of Determinative Bacteriology, 9th ed." (2000) Lippincott Williams & Wilkins, Philadelphia, 179-180; 186-187; and 566-567.

Ivnitski, D., et al., "Biosensors for detection of pathogenic bacteria." Biosens. Bioelectron. 14:599-624 (1999).

Janshoff, A. et al., "Piexoelectric mass-sensing devices as biosensors—an alternative to optical biosensors?" Angew. Chem. Int. Ed. (2000) 39:4005-4032.

Kanazawa, K.K., et al., "The oscillation frequency of a quartz resonator in contact with a liquid." Anal. Chim. Acta 175:99-105 (1985).

Kim, G.H., et al, "Impedance characterization of a piezoelectric immunosensor part I: Antibody coating and buffer solution." Biosens. Bioelectron. 18:83-89 (2003).

Kim, G.H., et al., "Impedance characterization of a piezoelectric immunosensor part II: *Salmonella typhimurium* detection using magnetic enhancement." Biosens. Bioelectron. 18:91-99 (2003).

Kim, N., et al., "Application of a flow-type antibody sensor to the detection of *Escherichia coli* in various foods." Biosens. Bioelectron. 18:1101-1107 (2003).

Lee, S.W., et al., "Determination of the viscoelastic properties of polymer films using a compensated phase-locked oscillator circuit." Anal. Chem. 74(1):125-131 (Jan. 1, 2002).

Li, Y. et al., "Immuno-nanobeads based QCM immunosensor for rapid, sensitive and specific detection of *E. coli* O157:H7," presented at 2005 Annual Meeting of the Institute of Biological Engineering (IBE) on Mar. 4-6, 2005 in Athens, Georgia, 5 pages.

Liu, F. et al., "QCM immunosensor with nanoparticle amplification for detection of *Escherichia coli* O157:H7," Sens. Instrumen. Food Qual. (2007) 8 pages.

Lu, C.S., et al., "Applications of Piezoelectric Quartz Crystal Microbalances" (1984) Elsevier, Amsterdam, 19-61.

Mao, X. et al., "A nanoparticle amplification based quartz crystal microbalance DNA sensor for detection of *Escherichia coli* O157:H7," Biosen. Bioelect. (2006) 21:1178-1185.

Martin, S.J., et al., "Characterization of a quartz crystal microbalance with simultaneous mass and liquid loading." Anal. Chem. 63(20):2272-2281 (Oct. 15, 1991).

Marx, K.A., "Quartz crystal microbalance: A useful tool for studying thin polymer films and complex biomolecular systems at the solution-surface interface." Biomacromolecules 4(5):1099-1120 (Sep./Oct. 2003).

Muramatsu, H., et al., "Piezoelectric immunosensor for detection of *Candida albicans* microbes." Anal. Chim. Acta 188:257-261 (1986).

Muramatsu, H., et al., "Computation of equivalent circuit parameters of quartz crystals in contact with liquids and study of liquid properties." Anal. Chem. 60(19):2142-2146 (Oct. 1, 1988).

Noël, M.A.M., et al., "High-frequency impedance analysis of quartz crystal microbalance. 1. General considerations." Anal. Chem. 66(4):484-491 (Feb. 15, 1994).

Olsen, E.V., et al., "Specific and selective biosensor for *Salmonella* and its detection in the environment." J. Microbiol. Meth. 53:273-285 (2003).

Pathirana, S.T., et al., "Rapid and sensitive biosensors for *Salmonella*." Biosens. Bioelectron. 15:135-141 (2000).

Rickert, J., et al., "QCM Operation in Liquids: Constant Sensitivity during Formation of Extended Protein Multilayers by Affinity." Anal. Chem. 69(7):1441-1448 (Apr. 1, 1997).

Sauerbrey, G.Z., "Verwendung von Schwingquarzen zur Wagung dunner Schichten und zur Mikrowagung" Zeitschrift fur Physik (1959) 155:206-222.

Su, X., et al., "A QCM immunosensor for *Salmonella* detection with simultaneous measurements of resonant frequency and motional resistance." Biosensors and Biolectronics 21:840-848 (2005).

Su, X., et al., "A QCM immunosensor with enhanced sensitivity for detection of *Salmonella typhimurium* in chicken carcass wash water." A poster presented at Food Safety Consortium/North Central Avian Disease Conference Joint Meeting, Oct. 3-5, 2004, Ames, Iowa.

Su, X., et al., "A nanoparticle- and silver-enhancement reaction-amplified microgravimetric biosensor." Chem. Commun. 755-756 (2001).

Su, X., et al., "A self-assembled monolayer-based piezoelectric immunosensor for rapid detection of *Escherichia coli* O157:H7." Biosens. Bioelectron. 19:563-574 (2004).

Su, X., et al., "An automatic quartz crystal microbalance immunosensor system for *Salmonella* detection." Presented orally at The 2004 Annual International Meeting of ASAE (The American Society of Agricultural Engineers) and CSAE (The Canadian Society of Agricultural Engineers) Aug. 1-4, 2004, Ottawa, Ontario, Canada. (PowerPoint presentation).

Tan, H., et al., "Robust complex non-linear regression method for the estimation of equivalent circuit parameters of the thickness-shear-mode acoustic wave sensor." Chemometrics Intell. Lab. Syst. 48:71-80 (1999).

Vaughan, R.D., et al., "Development of a quartz crystal microbalance (QCM) immunosensor for the detection of *Listeria* monocytogenes." Enzyme Microbiol. Technol. 29(10):635-638 (2001).

Xie, Q., et al., "A study of depletion layer effects on equivalent circuit parameters using an electrochemical quartz crystal impedance system." Anal. Chem. 71(20):4649-4656 (Oct. 15, 1999).

Xie, Q., et al., "A comparative study on the viscoelasticity and morphology of polyaniline films galvanostatically grown on bare and 4-aminothiophenol-modified gold electrodes using an electrochemical quartz crystal impedance system and SEM." Anal. Sci. 17:613-620 (May 2001).

Yang, M., et al., "Multiple chemical information from the thickness shear mode acoustic wave sensor in the liquid phase." Anal. Chem. 65(9):1158-1168 (May 1, 1993).

Zhou, T., et al., "The quartz crystal microbalance as a continuous monitoring tool for the study of endothelial cell surface attachment and growth." Biotechnol. Prog. 16:268-277 (2000).

United States Patent Office Action for U.S. Appl. No. 11/329,009 dated Nov. 20, 2006 (9 pages).

United States Patent Office Action for U.S. Appl. No. 11/329,009 dated May 16, 2007 (10 pages).

United States Patent Office Action for U.S. Appl. No. 11/329,009 dated Aug. 23, 2007 (3 pages).

Su, X.-L. et al., "Surface plasmon resonance and quartz crystal microbalance immunosensors for detection of *Escherichia coli* O157:H7," Transactions of the ASAE (2005) 48(1):405-413.

* cited by examiner

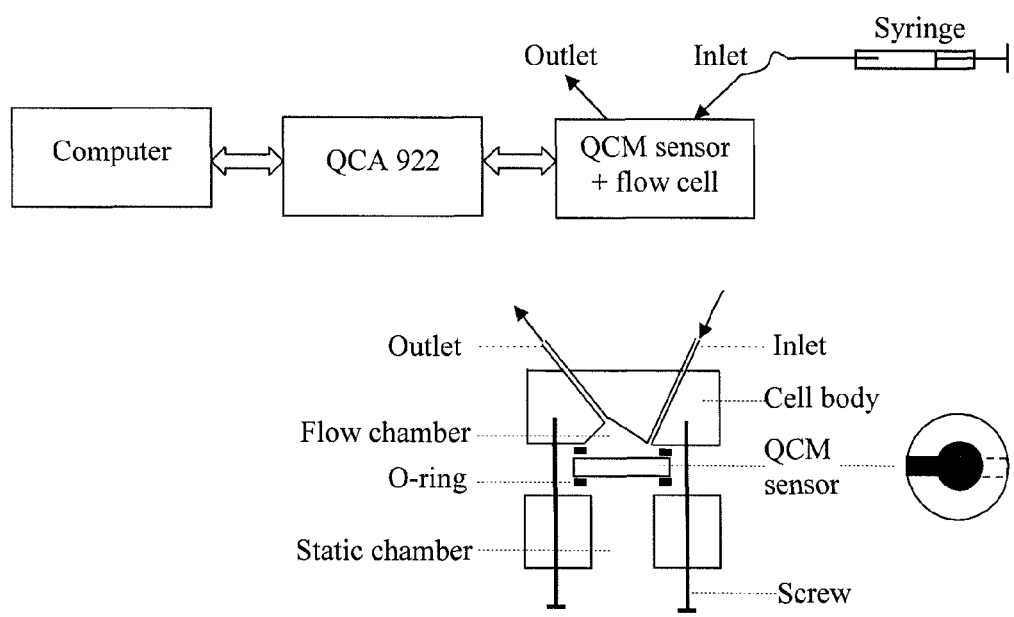
Fig. 1. Schematic diagram of the QCM test system (top) and vertical-sectional view of the flow cell (bottom).

Fig. 2. Typical conductance (solid line) and susceptance (dashed) spectra of the QCM. 1) blank QCM; 2) after adsorption of Protein A; 3) after antibody immobilization; and 4) after incubation with $10^8$ cells/ml of S. Typhimurium. All the spectra were obtained in PBS with the same quartz crystal.

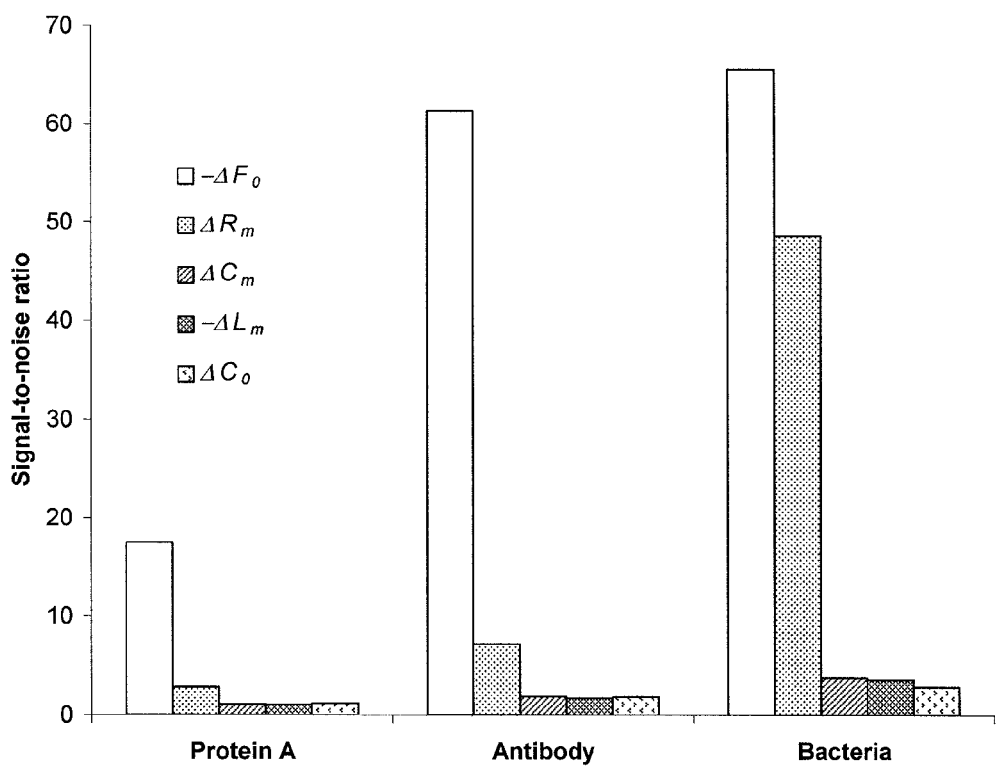
Fig. 3. Changes of $F_0$, $R_m$, $C_m$, $L_m$, and $C_0$ for the bindings of Protein A, antibody and bacteria, respectively.

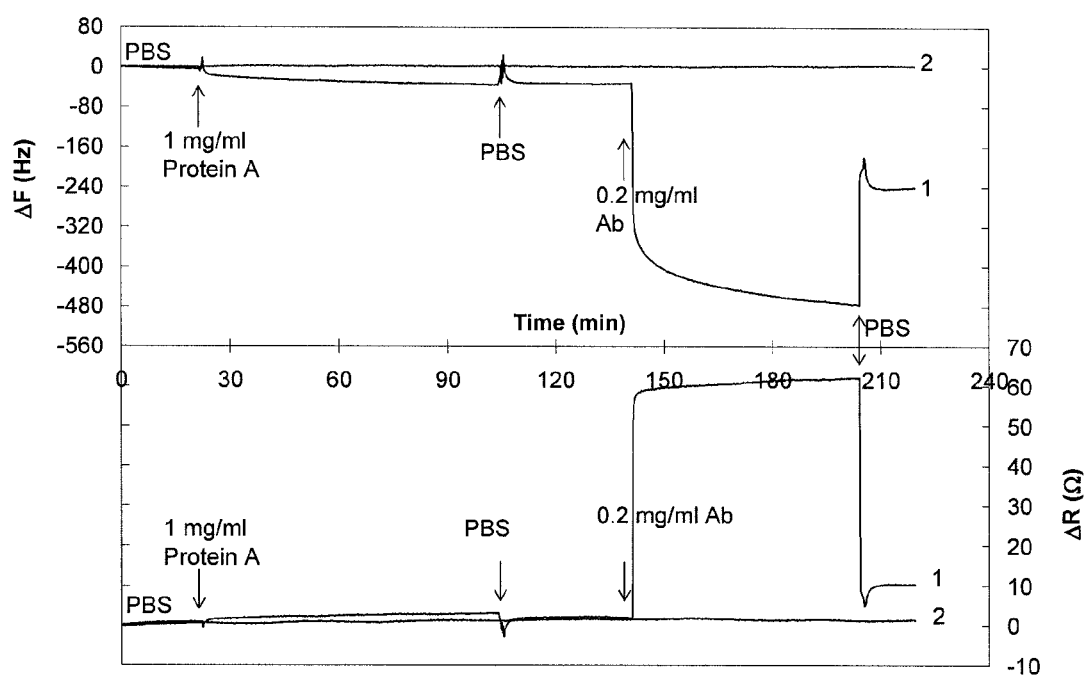
Fig. 4. Temporal responses of resonant frequency and motional resistance during antibody immobilization (1) and the prolonged baselines in PBS (2).

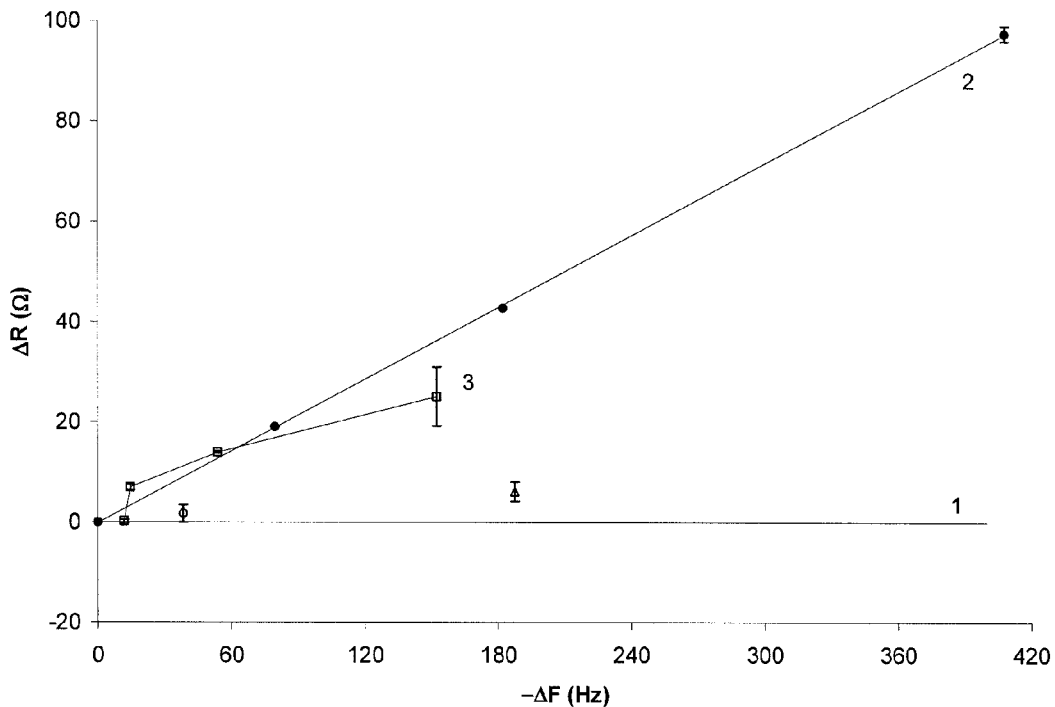

Fig. 5. The $\Delta F$–$\Delta R$ diagram for the layers of protein A (circle), antibody (triangle), and S. Typhimurium cells (squares). An elastic mass effect is represented by line 1, and a pure viscosity-density effect is represented by line 2, which was obtained with 0~20% sucrose solution. Line 3 shows the $\Delta F$–$\Delta R$ relationship for $10^5$-$10^8$ cells/ml of S. Typhimurium. Error bars represent standard deviations (n=3~6, the same below).

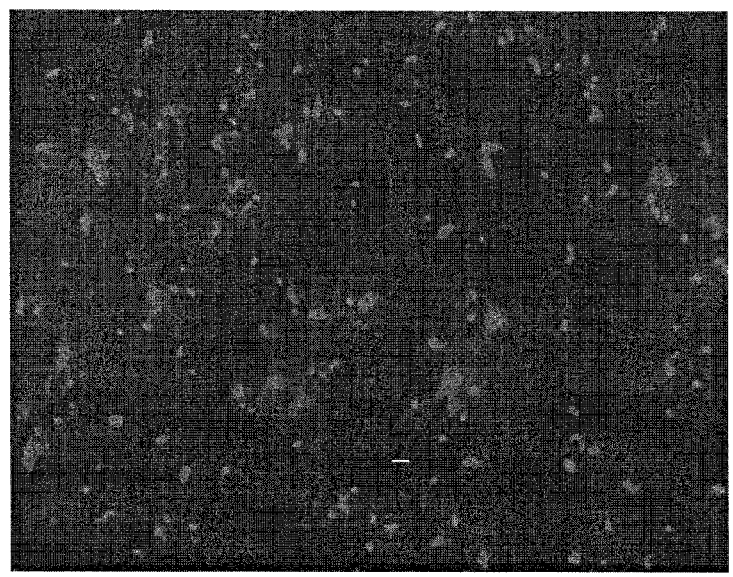
Fig. 6. Fluorescence image of a QCM surface with bound S. Typhimurium cells at $10^8$ cells/ml (bar = 4 μm).

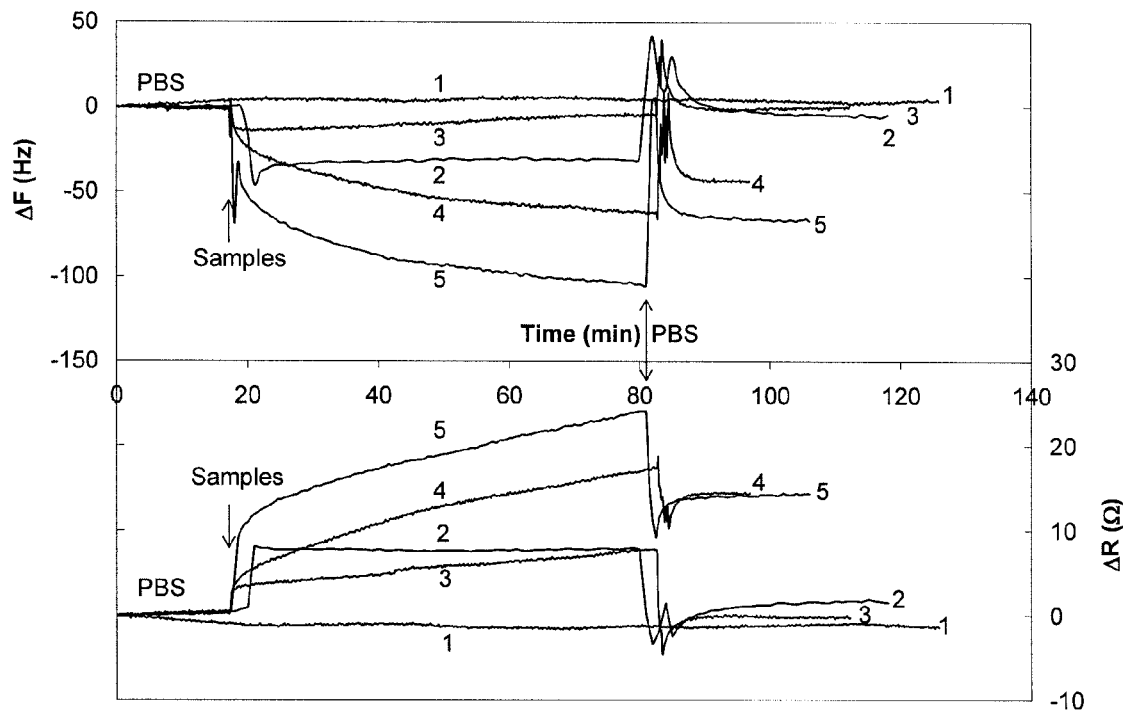
Fig. 7. Temporal responses of resonant frequency and motional resistance during bacterial detection without anti-*Salmonella* magnetic beads. 1) PBS; 2) Chicken meat sample; 3) $10^8$ cells/ml of *E. coli* K12 in PBS; 4) $10^7$ cells/ml of *S.* Typhimurium in PBS; 5) $10^7$ cells/ml of *S.* Typhimurium in chicken meat sample.

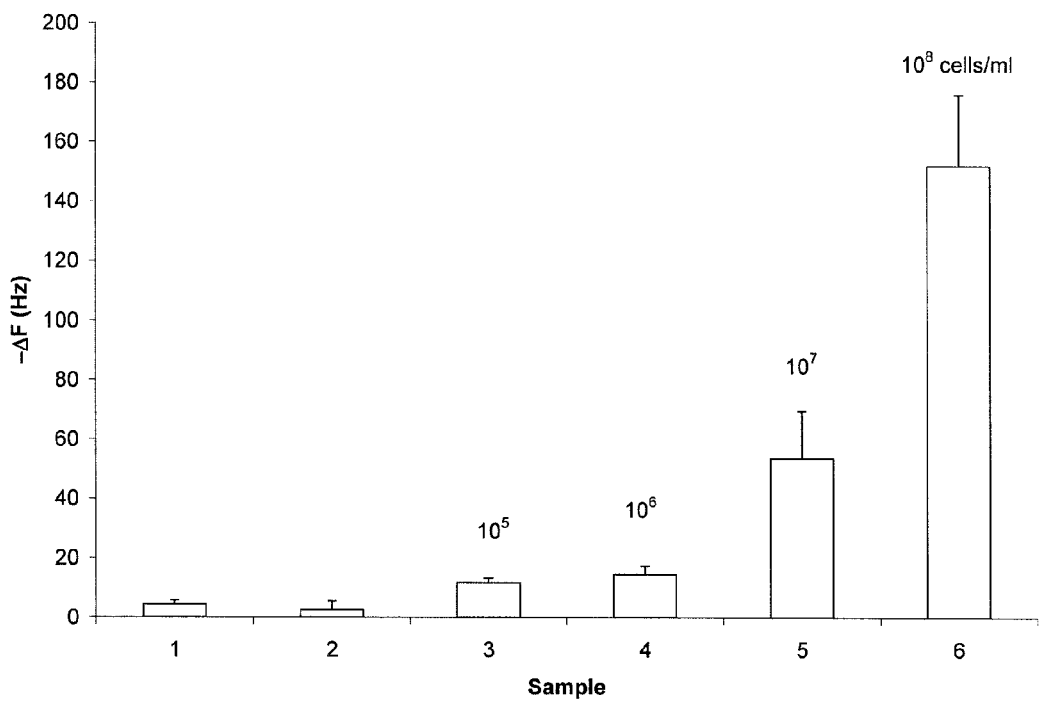
Fig. 8A. The change of resonant frequency as a function of the cell concentration. 1) Chicken meat sample; 2) $10^8$ cells/ml of *E. coli* K12; 3-6) $10^5$-$10^8$ cells/ml of *S.* Typhimurim. Error bars represent standard deviations (n=3~6).

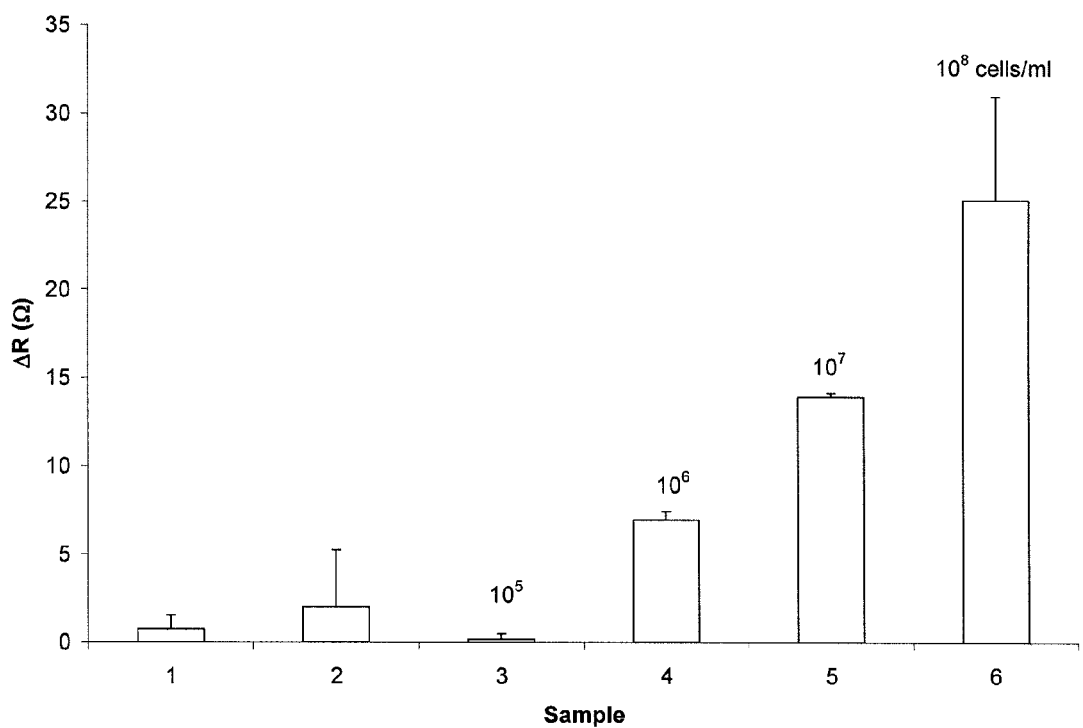
Fig. 8B. The change of motional resistance as a function of the cell concentration. 1) Chicken meat sample; 2) $10^8$ cells/ml of *E. coli* K12; 3-6) $10^5$-$10^8$ cells/ml of *S.* Typhimurim. Error bars represent standard deviations (n=3~6).

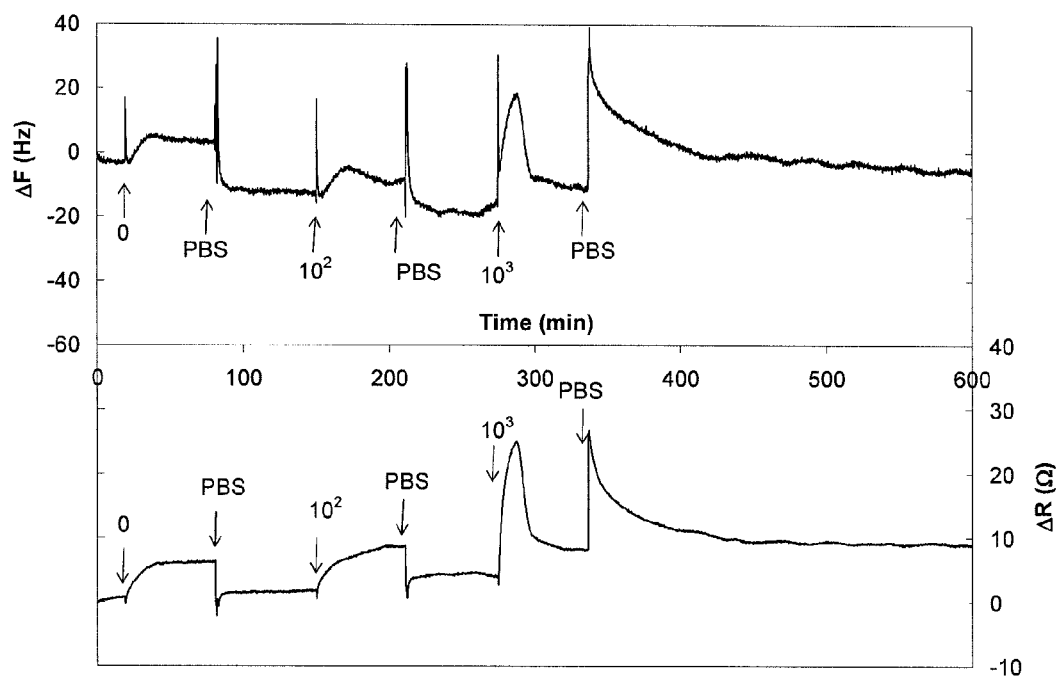
Fig. 9. Temporal responses of resonant frequency and motional resistance during bacterial detection with using anti-*Salmonella* magnetic beads. Numbers indicate concentrations (cells/ml) of *S.* Typhimurim in chicken meat sample.

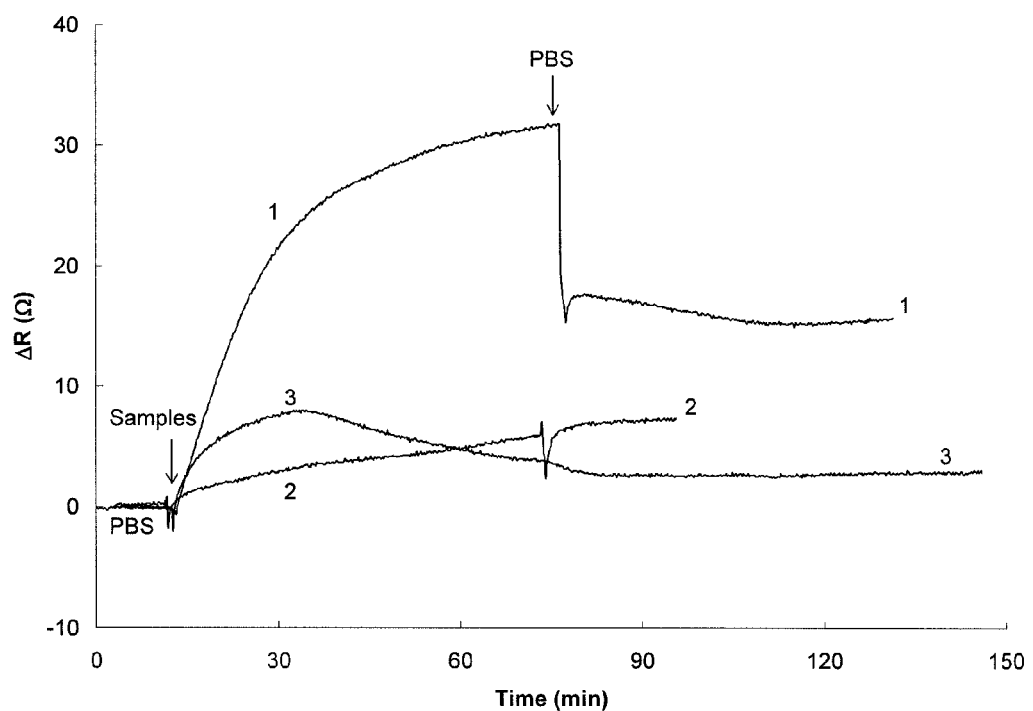
Fig. 10. Temporal responses of motional resistance of the QCM immunosensor (1 and 2) and blank QCM (3) for different samples. 1) $10^6$ cells/ml of *S.* Typhimurim + anti-*Salmonella* magnetic beads; 2) $10^6$ cells/ml of *S.* Typhimurim; 3) $10^7$ cells/ml of *S.* Typhimurim+ anti-*Salmonella* magnetic beads.

US 7,939,343 B2

METHOD FOR DETECTING AN UNKNOWN CONTAMINANT CONCENTRATION IN A SUBSTANCE

CROSS-REFERENCE TO RELATED APPLICATIONS

This application claims priority of U.S. provisional patent application No. 60/642,335, filed Jan. 7, 2005. This provisional application is incorporated herein by reference in its entirety. This application is a continuation of copending U.S. application Ser. No. 11/329,009, filed Jan. 9, 2006, which is herein incorporated by reference in its entirety.

STATEMENT REGARDING FEDERALLY SPONSORED RESEARCH

The invention was made with United States government support under Grant Number USDA/CREES 99-34211-7563 awarded by the United States Department of Agriculture. The United States government has certain rights in this invention.

BACKGROUND

Generally, quartz crystal microbalance (QCM) immunosensors for bacterial detection solely measure the resonant frequency, and the frequency shift is usually correlated to an elastic mass effect. The quartz crystal microbalance (QCM), as a simple yet powerful technique, has been widely employed in chemical and biological sensing. QCM can be designed as an immunosensor for directly detecting microorganisms without the need of labeled antibodies that are required in sandwich-type immunosensors. QCM immunosensors have been reported for rapid and specific detection of different bacteria. Most QCM immunosensors solely measure the resonant frequency ($F_0$) using the standard oscillator technique, and the frequency change ($\Delta F$) is usually explained by Sauerbrey equation, which states that the decrease in $F_0$($-\Delta F$) is linearly proportional to the increase in surface mass loading of QCM (Sauerbrey, 1959).

However, the Sauerbrey equation is applicable only to a thin (~1 μm) and elastic film coupled to the crystal surface, where the mass loading can be up to 0.05% of the crystal mass. The Sauerbrey equation does not apply to the case of cells attached to the QCM surface, largely due to the softness and relatively large size of the cells. In addition to the mass effect, the changes of surface viscoelasticity and other factors also contribute to the frequency change. Due to the additive nature of these effects, the mass effect cannot be differentiated from others when only $F_0$ is tracked.

High-frequency impedance/admittance analysis can provide more detailed information about the surface/interface changes of QCM. A QCM can be represented by a Butterworth-Van Dyke (BVD) model, which is composed of a static capacitance ($C_0$) in parallel with a motional branch containing a motional inductance ($L_m$), a motional capacitance ($C_m$), and a motional resistance ($R_m$) in series. These parameters are determined by physical properties of the quartz crystal, perturbing mass layer, and contacting liquid, and can be obtained with a high-frequency impedance analyzer by fitting the measured impedance/admittance data to the BVD model. A simpler way to provide insights into the viscoelastic properties of the bound surface mass is to simultaneously monitor $F_0$ and $R_m$ or $F_0$ and the dissipation factor D using a quartz crystal analyzer that is less expensive than the impedance analyzer. This method has been applied to study the behavior of adherent cells in response to chemical, biological, or physical changes in the environment.

The impedance analysis has been used to characterize a QCM immunosensor for detecting *Salmonella Typhimurium*. A magnetic force was utilized to collect the complexes of *Salmonella*-magnetic beads on the crystal surface, and $R_m$ was found the most effective and sensitive among the four circuit parameters, which offered a detection limit of about $10^3$ cells/ml. The sensitivity of the QCM immunosensor in the absence of magnetic beads has not been investigated nor has the measurements of $R_m$ and $F_0$, therefore it is unclear how much the magnetic beads could affect the detection sensitivity or which of the $F_0$ and $R_m$ measurements is superior in the presence or absence of the beads.

SUMMARY

In one embodiment the invention is a method for determining a concentration of a contaminant in a first sample, the method including producing the first sample, including adding a plurality of immuno-beads to a test substance; exposing a crystal microbalance immunosensor to the first sample; determining a change in a first motional resistance of the crystal microbalance immunosensor following exposure to the first sample ($\Delta R_1$); and determining the concentration of the contaminant in the first sample according to $\Delta R_1$.

In another embodiment the invention is a method for determining a concentration of a contaminant in a sample, including producing the sample, which includes adding a plurality of immuno-magnetic beads to a test substance; determining a change in a first motional resistance ($\Delta R_1$) of a crystal microbalance immunosensor exposed to the sample; and determining the concentration of the contaminant in the first sample according to $\Delta R_1$.

BRIEF DESCRIPTION OF THE DRAWINGS

FIG. 1 is a schematic diagram of the QCM test system (top) and vertical-sectional view of the flow cell (bottom).

FIG. 2 is a typical conductance (solid line) and susceptance (dashed) spectra of the QCM. 1) blank QCM; 2) after adsorption of Protein A; 3) after antibody immobilization; and 4) after incubation with $10^8$ cells/ml of *S. Typhimurium*. All the spectra were obtained in PBS with the same quartz crystal.

FIG. 3 is a bar graph of changes of $F_0$, $R_m$, $C_m$, $L_m$, and $C_0$ for the bindings of Protein A, antibody and bacteria, respectively.

FIG. 4 is a graph of temporal responses of resonant frequency and motional resistance during antibody immobilization (1) and the prolonged baselines in PBS (2).

FIG. 5 is a $\Delta F$-$\Delta R$ diagram for the layers of protein A (circle), antibody (triangle), and *S. Typhimurium* cells (squares). An elastic mass effect is represented by line 1, and a pure viscosity-density effect is represented by line 2, which was obtained with 0~20% sucrose solution. Line 3 shows the $\Delta F$-$\Delta R$ relationship for $10^5$-$10^8$ cells/ml of *S. Typhimurium*. Error bars represent standard deviations (n=3~6, the same below).

FIG. 6 is a fluorescence image of a QCM surface with bound *S. Typhimurium* cells at $10^8$ cells/ml (bar=4 μm).

FIG. 7 is a graph of temporal responses of resonant frequency and motional resistance during bacterial detection without anti-*Salmonella* magnetic beads. 1) PBS; 2) Chicken meat sample; 3) $10^8$ cells/ml of *E. coli* K12 in PBS; 4) $10^7$ cells/ml of *S. Typhimurium* in PBS; 5) $10^7$ cells/ml of *S. Typhimurium* in chicken meat sample.

FIG. 8(A) is a bar graph of change of resonant frequency as a function of the cell concentration FIG. 8(B) is a bar graph of change of motional resistance as a function of the cell concentration. 1) Chicken meat sample; 2) $10^8$ cells/ml of *E. coli* K12; 3-6) $10^5$-$10^8$ cells/ml of *S. Typhimurim*. Error bars represent standard deviations (n=3-6).

FIG. 9 is a graph of temporal responses of resonant frequency and motional resistance during bacterial detection with anti-*Salmonella* magnetic beads. Numbers indicate concentrations (cells/ml) of *S. Typhimurim* in chicken meat sample.

FIG. 10 is a graph of temporal responses of motional resistance of the QCM immunosensor (1 and 2) and blank QCM (3) for different samples. 1) $10^6$ cells/ml of *S. Typhimurim*+ anti-*Salmonella* magnetic beads; 2) $10^6$ cells/ml of *S. Typhimurim* without anti-*Salmonella* beads; 3) $10^7$ cells/ml of *S. Typhimurim*+anti-*Salmonella* beads.

DETAILED DESCRIPTION

Figure 11:
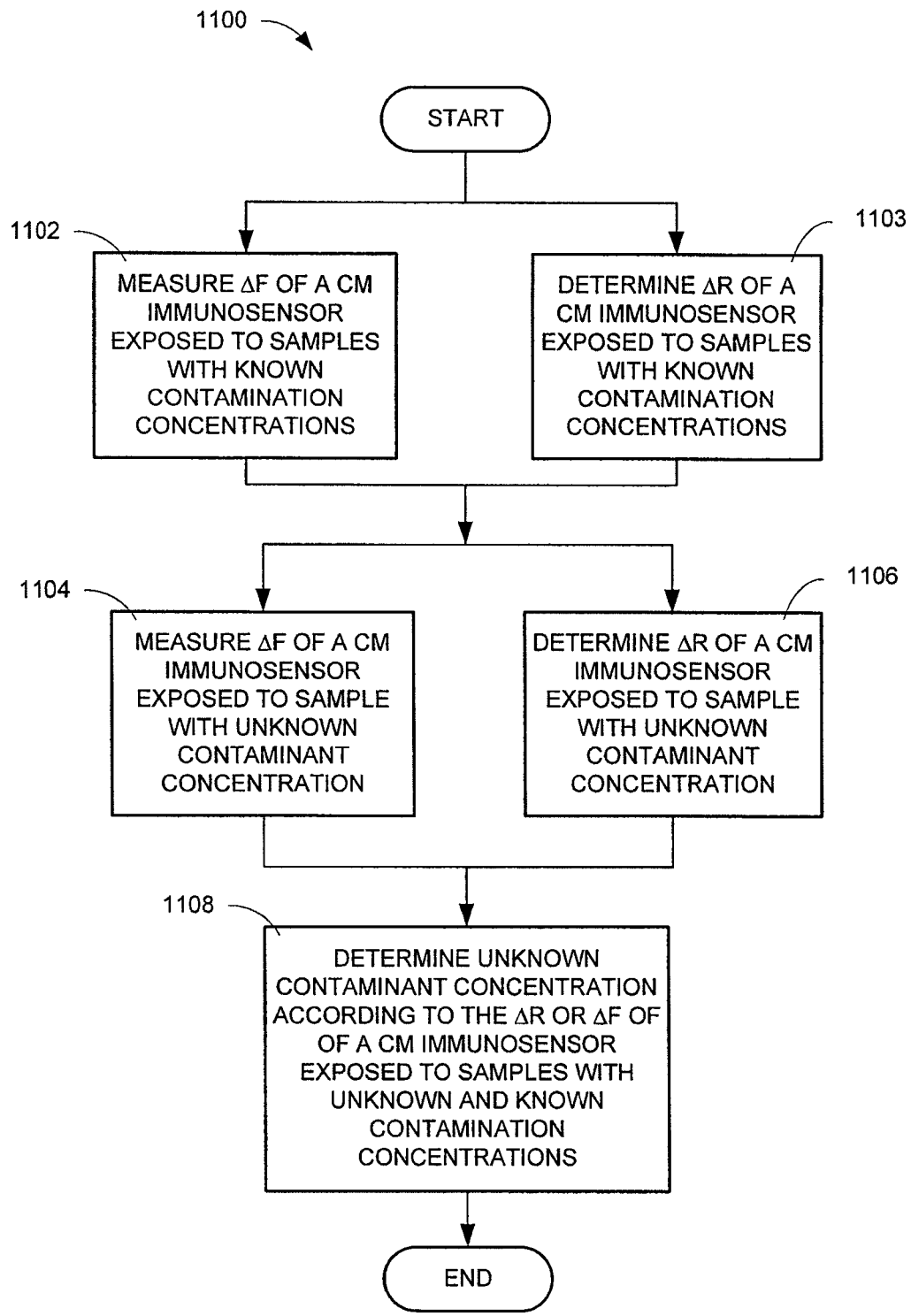
FIG. 11 is a block diagram of a method for detecting an unknown contaminant concentration in a substance.

A viscoelastic biosensor with enhanced sensitivity has been developed for the detection of bacterial pathogens such as *Salmonella Typhimurium* based on the use of immunomagnetic microbeads and the measurement of motional resistance. For *Salmonella Typhimurium*, the biosensor can be fabricated using Protein A for the antibody immobilization. High-frequency impedance analysis indicates that the changes in resonant frequency and motional resistance ($\Delta F$ and $\Delta R$) of the biosensor are significant while the changes in static capacitance, motional capacitance, and motional inductance are insignificant. $\Delta F$ and $\Delta R$ can be monitored simultaneously in real time during the biosensor fabrication and bacterial detection, and the $\Delta F$~$\Delta R$ diagram can be used to obtain insights into the surface characteristics. It is found that the immobilization of Protein A and antibody cause an elastic mass change while the binding of bacterial cells result in a viscoelastic change. In the direct detection of *S. Typhimurium* in food samples, $\Delta F$ and $\Delta R$ are proportional to the cell concentration in the range of $10^5$ to $10^8$, and $10^6$ to $10^8$ cells/ml, respectively. Using anti-*Salmonella* magnetic microbeads as a separator/concentrator for sample pretreatment as well as a marker for signal amplification, the detection limit is lowered to $10^2$ cells/ml based on the $\Delta R$ measurement. There is no interference from *E. coli* K12 and the sample matrix.

This method is developed for food safety, and can be used in food inspection and monitoring during food processing, storage and market. With minor modification, this method can be adopted for detection of other pathogenic bacteria in food samples, including *E. coli* O157:H7, *Listeria monocytogenes* and *Campylobacter jejuni*. In addition to immediate applications in the food area, the method can also be used in clinical or environmental applications.

Current quartz crystal microbalance (QCM) immunosensors for bacterial detection, with few exceptions, solely measure the resonant frequency, and the frequency shift is usually correlated to an elastic mass effect. In this study, a QCM immunosensor was described for the detection of bacterial pathogens such as *Salmonella Typhimurium* with simultaneous measurements of the resonant frequency and motional resistance. In the case of *Salmonella Typhimurium*, the immunosensor was fabricated using Protein A for the antibody immobilization. High-frequency impedance analysis indicated that the changes in resonant frequency and motional resistance ($\Delta F$ and $\Delta R$) of the QCM were significant while the changes in static capacitance, motional capacitance, and motional inductance were insignificant. $\Delta F$ and $\Delta R$ were monitored simultaneously in real time during the immunosensor fabrication and bacterial detection, and the $\Delta F$~$\Delta R$ diagram was used to obtain insights into the surface characteristics. It was found that the immobilization of Protein A and antibody caused an elastic mass change while the binding of bacterial cells resulted in a viscoelastic change. In the direct detection of *S. Typhimurium* in chicken meat sample, $\Delta F$ and $\Delta R$ were proportional to the cell concentration in the range of $10^5$ to $10^8$, and $10^6$ to $10^8$ cells/ml, respectively. Using anti-*Salmonella* magnetic beads as a separator/concentrator for sample pretreatment as well as a marker for signal amplification, the detection limit was lowered to $10^2$ cells/ml based on the $\Delta R$ measurements; however, $\Delta F$ was not related to the cell concentration. No interference was observed from *E. coli* K12 or the sample matrix.

EXAMPLE

In this example, $\Delta F$ and the change in $R_m$ ($\Delta R$) of a QCM immunosensor were approximately simultaneously monitored for the detection of *S. Typhimurium*. In addition, the immunosensor with food samples were evaluated and the effect of immuno-magnetic beads on the detection sensitivity was investigated.

Anti-*Salmonella* CSA-1 antibodies (1 mg) were manufactured by Kirkegaard & Perry Laboratories (Gaithersburg, Md.). Dynabeads® anti-*Salmonella* (diameter 2.8 µm) were obtained from Dynal Biotech Inc. (Lake Success, N.Y.). Protein A-soluble, from *S. aureus* (cowan strain) cell walls, was supplied by Sigma-Aldrich (St. Louis, Mo.). Propidium iodide (PI) was purchased from Molecular Probes (Eugene, Oreg.). Phosphate buffered saline (PBS, 0.01 M, pH 7.4) containing 0.138 M NaCl and 0.0027 M KCl, and 1% (w/v) bovine serum albumin (BSA)-PBS (pH 7.4) were received from Fisher Chemical (Fair Lawn, N.J.).

*Salmonella Typhimurium* (ATCC 14028) as a target pathogen, and *Escherichia coli* K12 (ATCC 29425) as a competing bacterium were obtained from American Type Culture Collection (Rockville, Md.). The pure culture of *S. Typhimurium* or *E. coli* K12 was grown in brain heart infusion (BHI) broth (Remel, Lenexa, Kans.) at 37° C. for 20 h before use. The culture was serially diluted with physiological saline solution and the viable cell number was determined by conventional plate counting. *S. Typhimurium* was enumerated by surface plating on xylose lysine tergitol ($XLT_4$) agar (Remel, Lenexa, Kans.). *E. coli* K12 was enumerated using sorbitol-MacConkey (SMAC) agar (Remel, Lenexa, Kans.). The undiluted cultures were heated in a 100° C. water bath for 15 min to kill all bacteria, and then diluted with PBS or sample solution to desired concentrations for further use.

Chicken breast meat purchased from a local grocery store was used as a tested sample. An amount of 25 g chicken meat was put into a Whirl-plastic bag (Nasco, Fort-Atkinson, Wis.) containing 225 ml of 0.1% buffered peptone water (Difco, Detroit, Mich.) and stomached on a Seward 400 stomacher (Seward, UK) for 2 min. The mixture was filtered by cheesecloth and then centrifuged to remove large debris and particles. An aliquot of 9 ml of the resulting meat solution was added with 1 ml of $10^9$ cells/ml of heat-killed *S. Typhimurium* to make a sample solution of $10^8$ cells/ml, which was further serially diluted to the desired concentration with the meat solution.

The inoculated sample solutions were analyzed using the QCM immunosensor directly without any other treatment or after immuno-magnetic separation (IMS). In IMS, a total of 20 μl of anti-*Salmonella* beads (ca. 0.1 mg or $6.6 \times 10^6$ beads) and 1.0 ml of sample solution containing $0 \sim 10^7$ cells/ml of *S. Typhimurium* were added into micro-centrifuge tubes and vortexed for several seconds. The mixture was incubated at room temperature for 60 min with a gentle mixing. Then, the micro-centrifuge tubes were loaded into MPC-S magnetic particle concentrators (Dynal Biotech) and allowed 3 min for separating the magnetic beads from the liquid matrices. The liquid part was discarded and the resulting immuno-complexes of beads and target bacteria were resuspended in 250 μl PBS for further test with the QCM immunosensor.

The immunosensor was fabricated by immobilizing anti-*Salmonella* antibodies on the gold surface of AT-cut quartz crystals (International Crystal Manufacturing, Oklahoma City, Okla.), which had a diameter of 13.7 mm, a polished Au electrode (5.1 mm diameter, 1,000 Å thickness) deposited on each side, and a resonant frequency of 7.995 MHz. The crystals were pretreated with 1 M NaOH for 20 min and 1M HCl for 5 min in sequence to obtain a clean Au surface. After each pretreatment the crystals were rinsed by spraying ethanol and water successively, and dried in a stream of nitrogen. Each of the resulting crystals was mounted on a 70-μl acrylic flow cell (International Crystal Manufacturing) as shown in FIG. 1 with only one face exposed to the solution. ΔF and ΔR were simultaneously monitored in real time during antibody immobilization and *S. Typhimurium* detection using a QCA922 quartz crystal analyzer (Princeton Applied Research, Oak Ridge, Tenn.).

Protein A method was used for the antibody immobilization. First the crystal was flushed with 1 ml PBS to obtain a stable baseline. Secondly, the detection chamber was overflowed by 500 μl of 1 mg/ml Protein A. After 1 h incubation, the detection chamber was flushed with 1 ml PBS 5 times to rinse off the excess Protein A and to obtain a stable baseline. Thirdly, the chamber was overflowed by 500 μl of 200 μg/ml anti-*Salmonella* antibody solution. Also after 1 h incubation, the chamber was flushed with 1 ml PBS 5 times to rinse off the unimmobilized antibodies and to obtain a stable baseline. All the baselines were obtained in PBS at a stop-flow mode, and the differences between every two neighboring baselines were calculated as the net responses caused by the immobilization of Protein A and antibodies, respectively.

The QCM immunosensor was tested in a stop-flow mode for the detection of *S. Typhimurium* in PBS or chicken meat sample. First, the immunosensor was incubated with 1% BSA-PBS, blank chicken meat sample solution or $10^8$ cells/ml of *E. coli* K12 solution for 1 h to block nonspecific binding sites. Then the QCM was flushed with 1 ml PBS 5 times to obtain a stable baseline. Following this, the chamber was overflowed by 1 ml (without magnetic beads) or 250 μl (with magnetic beads) of sample solution. After incubation for 1 h, the chamber was flushed with 1 ml PBS 5 times to rinse off nonspecific bindings and to obtain a stable baseline. The difference between the two PBS baselines, both obtained in a stop-flow mode, was correlated to the concentration of *S. Typhimurium* in the sample solution.

All the experiments were conducted at room temperature, and disposable 1-ml syringes were used to push the reagent/sample solution through the detection chamber.

The QCM sensor was connected to an HP 4291A impedance analyzer (Hewlett Packard Japan, Hyogo, Japan) via an HP 16092A test fixture. The conductance and susceptance spectra (G~f and B~f) were measured simultaneously under a linear frequency sweep mode with 201 frequency points and a frequency span of 10 kHz covering the resonant frequency. The measured G~f and B~f data were fitted to the BVD model using the following equations (Tan et al., 1999), $$G(\omega) = \frac{R_m}{R_m^2 + L_m^2(\omega - \omega_0^2/\omega)^2} \quad (1)$$

$$B(\omega) = \omega C_0 - \frac{L_m(\omega - \omega_0^2/\omega)}{R_m^2 + L_m^2(\omega - \omega_0^2/\omega)^2} \quad (2)$$

where $\omega = 2\pi f$, f is scanning frequency, $\omega_0 = 2\pi F_0$, and $F_0$ is the resonant frequency ($F_0 = (2\pi\sqrt{L_m C_m})^{-1}$). The fittings, which involved minimizing the relative sum of the residual square (Xie et al., 1999) with $R_m$, $L_m$, $C_0$, and $F_0$ as estimated parameters, were executed using the Excel Microsoft Solver tool. $C_m$ was calculated from $F_0$ and $L_m$. Typical fitted results of $F_0$, $R_m$, $L_m$, $C_m$, and $C_0$ were 7992987.4 Hz, 9.625 Ω, 17.897 mH, 22.154 fF, and 8.243 pF (including parasitic capacitance in the test fixture) for an unperturbed quartz crystal placed in the air, and 7991347.7 Hz, 346.3 Ω, 25.394 mH, 15.620 fF, and 10.738 pF for a bare crystal (mounted on the flow cell) in PBS, respectively. The values of $R_m$, $L_m$ and $C_m$ obtained in the air are close to those calculated from the equations (25b-d) of Martin et al (1991) with the relative deviations ranging between 1.5~19%.

The fluorescence images were taken on Nikon Eclipse 600 Fluorescent Microscope (Nikon Instruments, Lewisville, Tex.) using the Nikon G-2A filter set. Before fluorescent microscopy, the QCM immunosensor was incubated with $10^8$ cells/ml of *S. Typhimurium* for 1 h. After being rinsed off non-specific bindings, the QCM surface was treated with 1% PI for 2 h to stain the specifically bound cells.

Although extensively used in surface/interface studies, the high-frequency impedance/admittance has been rarely applied to characterize the QCM immunosensor for bacterial detection. In this study, the QCM immunosensor was characterized step by step with the admittance analysis. FIG. 2 shows typical conductance (G) and susceptance (B) spectra of the same quartz crystal subjected to different treatments. All the spectra were measured in PBS after physical adsorptions had been rinsed off. It was demonstrated that both the maximum G ($G_{max}$) and the frequency at $G_{max}$ decreased with the layers of protein A, antibody and bacterial cells being deposited on the QCM surface successively. The decreased values obtained from FIG. 1A are Ca. 0.009, 0.029, and 0.218 mS for the $G_{max}$ and 50, 200, and 200 Hz for the frequency at $G_{max}$, respectively.

To acquire insights into the properties of the films deposited on the QCM surface, the measured admittance data were fitted to the BVD model to extract the values of the four equivalent circuit parameters $C_0$, $L_m$, $R_m$, and $C_m$ along with $F_0$. Each equivalent circuit parameter has its distinct physical meaning (Martin et al., 1991; Buttry and Ward, 1992): $C_0$ reflects the dielectric properties between the electrodes located on opposite sides of the insulating quartz crystal; $C_m$ represents the energy stored during oscillation, which corresponds to the mechanical elasticity of the vibrating body; $L_m$ is related to the displaced mass; and $R_m$ is the energy dissipation during oscillation, which is closely related to viscoelasticity of the deposited films and viscosity-density of the adjacent liquid (Muramatsu et al., 1988; Lee et al., 2002). The changes of these parameters are illustrated in FIG. 3 in terms of the signal-to-noise (S/N) ratio. The noise levels of $F_0$, $R_m$, $C_m$, $L_m$, and $C_0$, defined as the overnight variations in PBS, were 2.6 Hz, 0.62 Ω, 0.0064 fF, 0.0039 mH, and 0.0068 pF, respectively. As shown in FIG. 3, in all cases including Protein A adsorption, antibody immobilization, and bacterial binding, the change of $F_0$ was the largest and the change of $R_m$ was the second while the change of $C_m$, $L_m$, and $C_0$ were insignificant with the S/N≦3. The same result was obtained in a repeated test using another quartz crystal. According to Martin et al. (1991), both $R_m$ and $L_m$ increase with simultaneous mass and liquid loading while $C_0$ and $C_m$ are kept unchanged. $L_m$ did not increase as expected, and this was likely due to the high correlation between $L_m$ and $C_m$ and the difficulty in accurate measurement of $L_m$ (Yang and Thompson, 1993; Noel and Topart, 1994). Kim et al. (2003a) also observed a decrease in $L_m$, and they corrected the $L_m$ as follows (Yang and Thompson, 1993), $$(L_m)_{Corrected} = \frac{(L_m C_m)_{liquid}}{(C_m)_{unloaded}} \qquad (3)$$

where the corrected $L_m$ is calculated based on the assumption that $C_m$ is a constant. Since $F_0 = (2\pi\sqrt{L_m C_m})^{-1}$, the corrected $L_m$ reflects the same information of $F_0$, and therefore it is not discussed below while $F_0$ and $R_m$ are discussed. FIG. 4 shows simultaneous response courses of ΔF and ΔR during the surface modification with Protein A and antibodies successively along with the prolonged baselines in PBS. The surface modification was conducted in the stop-flow mode and PBS was used to rinse off physical adsorptions. To eliminate the background interference, a stable baseline was obtained in PBS before and after the injection of Protein A and antibodies, and the difference between every two neighboring baselines was calculated as the net response caused by the immobilization of Protein A and antibodies, respectively. Similar to the results of the above admittance analysis, the net response of $F_0$ is more obvious than that of $R_m$ by comparing the S/N ratios.

Simultaneous measurements of Δt and ΔR can differentiate an elastic mass effect from the viscosity-induced effects. ΔR is a good measure of the viscoelastic change. For an elastic mass change, ΔR will be zero and ΔF will be linearly proportional to the mass change in accordance with the Sauerbrey equation. For a QCM with only one side in contact with a Newtonian liquid, both ΔF and ΔR are linearly proportional to the squared root of the product of viscosity and density of the liquid. Hence, a pure viscosity-density change will result in a linear ΔF~ΔR plot. As illustrated in FIG. 5, the elastic mass effect can be represented by line 1 where ΔR=0, and the pure viscosity-density effect can be represented by line 2, which was obtained with 0~20% sucrose solution and had a slope of 0.24 Ω/Hz. In the presence of a viscoelastic change, the ΔR~ΔF plot will lie between the lines 1 and 2 or even above the line 2. For co-existence of mass and viscosity-induced changes, the absolute value of ΔR/ΔF will be <0.24 Ω/Hz. In general, the smaller the absolute value of ΔR/ΔF, the more predominant the elastic mass effect. The ΔR~ΔF data obtained in each step including those for specific bacterial bindings, which will be described later in more details, are presented in FIG. 5 to identify an elastic or viscoelastic change. The net responses of ΔF and ΔR caused by the coating of Protein A were −38.3±7.9 Hz (mean±S.D., n=3) and 1.7+ 0.5 Ω, respectively, and the ratio of ΔR to −ΔF was 0.04 Ω/Hz, much smaller than 0.24 Ω/Hz. Considering the ΔR measurement in PBS had a noise level of ~1 Ω, the above ΔR change was approximately negligible, and the ΔF change caused by the adsorption of Protein A was attributed to an elastic mass effect. Corresponding to the immobilization of antibodies, the net responses of ΔF and ΔR were −187.6±17.0 Hz (mean±S.D., n=6) and 6.1±1.9 Ω, respectively. Although an obvious ΔR increase was observed, the ratio of ΔR to −ΔF was only 0.03 Ω/Hz, also much smaller than 0.24 Ω/Hz. Hence, the ΔF change caused by the adsorption of antibodies was also primarily due to an elastic mass effect. Therefore, the Sauerbrey equation could be applied to estimate the surface coverages of Protein A and antibodies, which were calculated to be 0.26±0.05 and 1.28±0.12 μg/cm², respectively.

The ΔR~ΔF data for the binding of *Salmonella* cells is displayed as line 3. At 10⁵ cells/ml, the ΔF change was obvious but the ΔR change was negligible, indicating an elastic mass effect. When the cell concentration was higher than 10⁶ cells/ml, both a negative ΔF shift and a positive ΔR shift were observed, and the ratio of ΔR to −ΔF was as high as 0.16~0.48, close to or larger than the slope of the pure viscosity-density response line (line 2). Thus, the layer of bound cells was viscoelastic and the ΔF response did not obey the Sauerbrey equation. Such viscoelastic changes were also observed on certain polymeric films and cells (Zhou et al., 2000).

FIG. 6 shows typical fluorescence image of the QCM surface after it was incubated with 10⁸ cells/ml of *S. Typhimurium* and stained with PI, a nucleic acid stain for deal cells. The distribution of *S. Typhimurium* cells is roughly uniform, indicating an approximately homogenous immunosensing surface. The surface coverage of the bound cells was measured to be ca. 9×10³ cells/mm².

The QCM immunosensor was tested in a stop-flow mode for direct detection of *S. Typhimurium* in PBS as well as in the stomaching solution of chicken meat without using magnetic beads. Typical responses of ΔF and ΔR are given in FIG. 7. Also non-specific bindings were rinsed off by PBS and the interference from sample matrixes was excluded by obtaining a stable PBS baseline before and after the injection of sample solutions. The difference between two adjacent baselines was calculated as the net response induced by specifically bound bacteria. The net responses of ΔF and ΔR caused by 10⁷ cells/ml of *S. Typhimurium* in PBS (curve 4) or in chicken meat sample (curve 5) were both significantly distinguishable from the negative controls (curves 1~3). For 10⁷ cells/ml of *S. Typhimurium*, the net response of ΔR in PBS and that in the chicken meat sample were almost the same, but the net response of ΔF in the chicken meat sample was greater than that in PBS, which might be ascribed to the sensor-to-sensor variations and/or the difference of sample backgrounds. Although the QCM surface was pre-saturated with a blank solution of the chicken meat sample to depress the nonspecific bindings of the sample matrix, the *Salmonella* cells might carry some food debris or particles and therefore caused lager ΔF response.

The calibration data for the detection of *S. Typhimurium* in an inoculated chicken meat sample based on the measurements of ΔF and ΔR are presented in FIGS. 8A and 8B, respectively. Chicken meat was selected as a representative sample of poultry product, one of the major vehicle foods of *S. Typhimurium*. As can be seen, the net responses of ΔF and ΔR were proportional to the concentration of *S. Typhimurium* in the range of 10⁵ to 10⁸, and 10⁶ to 10⁸ cells/ml, respectively.

The ΔR measurement was more sensitive than the ΔR measurement in terms of the detection limit (FIG. 8) as well as in the S/N ratio (FIG. 3). This might be due to the fact that both elastic and viscoelastic mass change resulted in a negative ΔF while the former does not cause a change of ΔR. The layer of the bound *Salmonella* cells is viscoelastic, but a small portion of the cells can still be probed as an elastic mass.

The relative standard deviations of the sensor-to-sensor determinations varied between 12~29% (n=3~6) for the ΔF measurement and 1.5~28% for the ΔR measurement, respectively. The sample matrix did not interfere with the detection of *S. Typhimurium* in both the ΔF and ΔR measurements, nor did *E. coli* K12 although at a concentration as high as $10^8$ cells/ml.

The QCM immunosensors for bacterial detection reported previously typically have a detection limit ranging between $10^5$ and $10^7$ cells/ml and a detection time of minutes to several hours. In this study, without using magnetic beads, a detection limit of $10^5$~$10^6$, cells/ml was obtained for the direct detection of *S. Typhimurium*. However, the infectious dosage of a foodborne pathogen such as *S. Typhimurium* can be as low as 15-20 cells.

In this example, the effect of magnetic beads was investigated in different ways: the magnetic force was only used for separating the *Salmonella*-bead complexes from sample matrix, the bead complexes were inducted to the QCM surface simply using a syringe, and ΔF and ΔR were simultaneously monitored in real time. This avoided the use of a complicated test chamber with a magnet and an ultrasonic transducer and the inconvenience of discontinuous impedance measurements.

FIG. 9 shows typical temporal responses of ΔF and ΔR for the detection of *S. Typhimurium* in chicken meat sample using anti-*Salmonella* magnetic beads.

A firm and tight attachment of bacteria causes a negative ΔF, in contrast, a flexible attachment results in a positive ΔF. In the absence of anti-*Salmonella* magnetic beads, the former case applied as the specific binding of *Salmonella* cells always led to a negative ΔF that was proportional to the cell concentration. In the presence of anti-*Salmonella* beads, however, ΔF was not related to the cell concentration and was either positive or negative even at the same cell concentration. This was probably because the size of the *Salmonella*-bead complexes was not uniform from sample to sample. *S. Typhimurium* is a straight rod bacterium. Typically, the width of a *Salmonella* cell is 0.7-1.5 μm and its length is 2-5 μm. The magnetic beads used had a diameter of 2.8 μm. The size of the *Salmonella*-bead complexes thus varied from several microns to tens of microns. Small complexes might generate a tight attachment and a negative ΔF, and oppositely, large complexes and aggregates could cause a flexible attachment and positive ΔF.

A significant net increase in ΔR was always observed at a cell concentration higher than $10^2$ cells, and the net response increased with increasing cell concentration. The effect of anti-*Salmonella* magnetic beads can be seen more clearly in FIG. 10. The background interference was eliminated by achieving a stable baseline in PBS before and after the sample injection. At the same cell concentration of $10^6$ cells/ml, the net change of ΔR in the presence of anti-*Salmonella* magnetic beads (curve 1) was positive and 2 times that in the absence of anti-*Salmonella* beads (curve 2). The blank QCM (without immobilized antibodies) did not give a significant increase in ΔR although tested at a higher cell concentration of $10^7$ cells/ml with anti-*Salmonella* beads (curve 3). The detection limit based on the ΔR measurement was ca. $10^2$ cells/ml, and this was 1,000 and 10,000 times lower than those of the ΔF and ΔR measurements without magnetic beads, respectively. The improvement of detection sensitivity is attributed to the dual roles of magnetic beads. As a separator/concentrator, the beads separated the target bacteria from the sample matrix and concentrated the sample solution. As a marker, the beads amplified signals of ΔR measurement through increasing the surface viscoelasticity.

ΔF measurement is more sensitive than the ΔR measurement in the direct detection of *S. Typhimurium*. When magnetic beads were used, however, the ΔR measurement was more reliable, and the sensitivity was improved by 1,000~10,000 times. The detection limit based on the ΔR measurement was approximately $10^2$ cells/ml, lower than those of the most reported QCM immunosensors for bacterial detection. It was also shown that simultaneous measurement of ΔF and ΔR could provide insights into the surface characteristics: the layers of immobilized Protein A and antibodies were dominantly elastic, the layer of specifically bound *Salmonella* cells was viscoelastic, and the magnetic beads might increase the viscoelasticity. The QCM immunosensor was successfully applied to the analysis of inoculated food samples with negligible interference form *E. coli* K12 and the sample matrix.

The same principle can be applied to detect other pathogenic bacteria in food, environmental and clinical samples using specific primary antibodies and immuno-magnetic beads. For example, it can be used to detect infectious bacteria in human blood and urine samples, and pathogenic bacteria in water of rivers, wells and reservoirs. It provides a rapid, sensitive, specific, inexpensive and portable biodetection method for applications in food safety and security, environmental protection and clinical diagnoses.

In addition to the microbeads, immuno-magnetic nanobeads and other types of magnetic beads can be used in this procedure for a QCM immunosensor in the detection of various pathogens. The similar detection limit, time, specificity and sensitivity are expected.

As mentioned above, QCM immunosensors, and crystal microbalance (CM) immunosensors in general, may be used in detecting contaminants in a substance. These contaminants include pathogens, bacteria, viruses, insects, arachnids and other undesirable items. An example of such a method is shown in FIG. 11. The method 1100 illustrated in FIG. 1 may be used to measure samples of a substance. The samples may include some type of immuno-bead such as, as magnetic, micro, nano and any combination of such.

As shown in FIG. 11, the method 1100 generally includes measuring the change in frequency (ΔF) 1102 and determining change in motional resistance (ΔR) 1103 of a CM immunosenor exposed to various samples that include known concentrations of a contaminant of interest. The method 1100 further includes measuring the ΔF and determining the ΔR of a CM immunosensor exposed to a sample containing the contaminant of interest at an unknown concentration. The measurements of ΔF create data that relate a given ΔF to a known contaminant concentration. Likewise, the determinations of ΔR create data that relate a given ΔR to a known contaminant concentration. The unknown contaminant concentration may be determined according to the ΔF of the samples with the known and unknown contaminant concentrations or the ΔR of the samples with the known and unknown contaminant concentrations 1108. Steps 1102, 1103, 1104, and 1106 may be performed in any order. For example, steps 1102 and 1103 may be performed simultaneously. In another example, steps 1104 and 1106 may be performed simultaneously.

Figure 12:
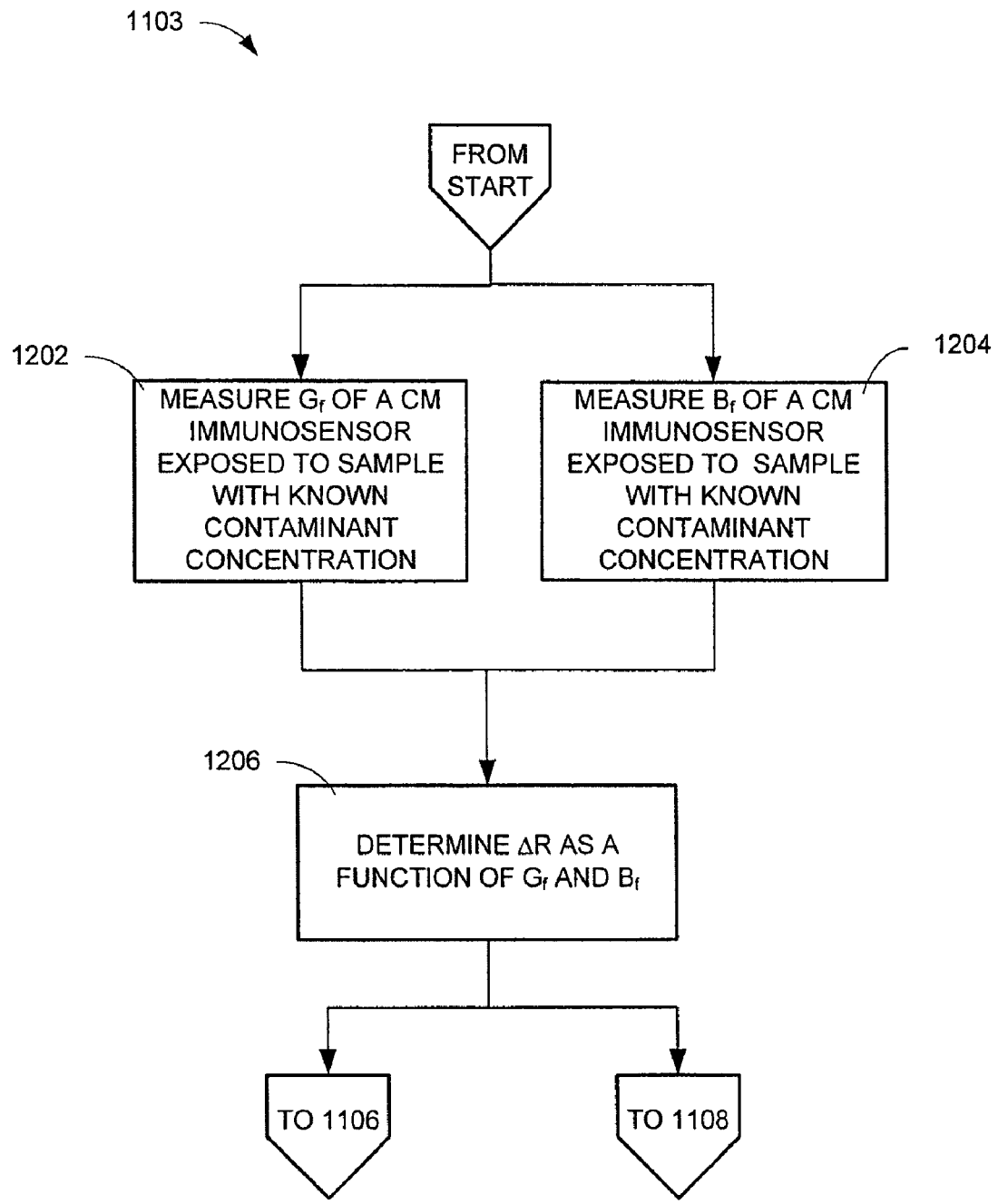
FIG. 12 is a block diagram of a method for determining a change in resistance of a CM immunosensor exposed to samples with known contaminant concentrations.

ΔF of a CM immunosensor exposed to samples with the known and unknown contaminant concentrations 1102, 1104, respectively, may be measured directly. ΔR of a CM immunosensor exposed to a sample containing the known or unknown contaminant concentration 1103, 1106, respectively, may be determined by direct measurement. For example, the ΔR may be measured directly using a QCA 922. ΔR may also be measured indirectly, an example of which is shown in FIG. 12. Although FIG. 12 refers to determining ΔR of a CM immunosensor exposed to a sample containing the known contaminant concentration 1103, the method shown is equally applicable to determining the ΔR of a sample containing the unknown contaminant concentration 1106.

Referring to FIG. 12, ΔR may be determined indirectly by measuring the conductance spectrum ($G_f$) 1202 and susceptance spectrum ($B_f$) 1204 of the CM immunosensor exposed to the sample with the known contaminant concentration. An example of a manner by which these measurements may be made is discussed above. After $G_f$ and $B_f$ have been measured 1202, 1204, ΔR may be determined as a function of $G_f$ and $B_f$ 1206. For example, ΔR may be determined 1206 by fitting $G_f$ and $B_f$ to the BVD model using equations (1) and (2) or a modified BVD model.

As shown in FIG. 11, the unknown contaminant concentration may be determined according to the ΔR of the CM immunosensor exposed to the samples with the known contaminant concentrations and the ΔR of the sample with the unknown contaminant concentration 1108. Alternately, the unknown contaminant concentration may be determined according to ΔF of the CM immunosensor exposed to the samples with the known contaminant concentrations and the ΔF of sample with the unknown contaminant concentration 1108. The determination of the unknown contaminant concentration is shown in more detail in FIG. 13.

Figure 13:
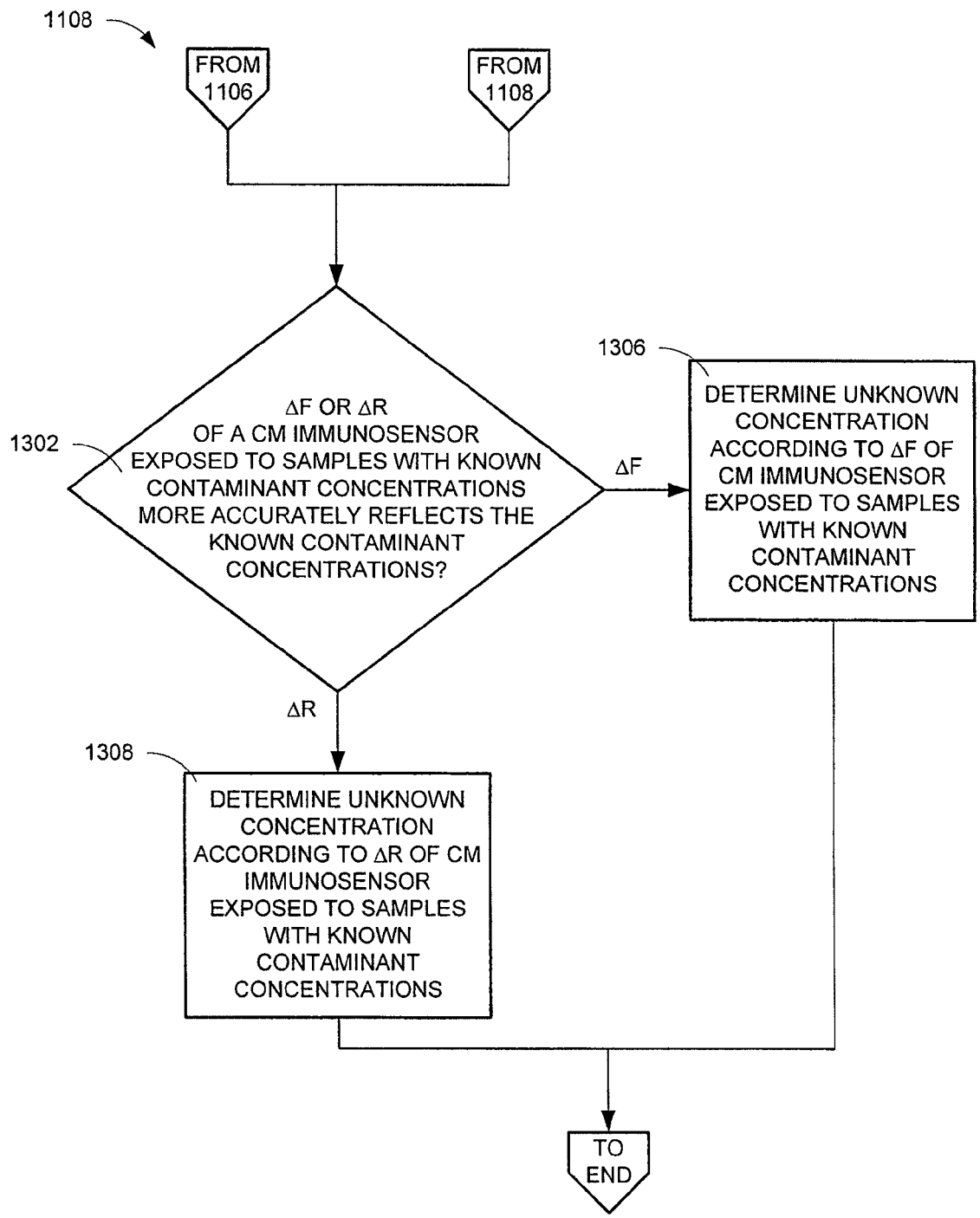
FIG. 13 is a block diagram of a method for determining an unknown contaminant concentration in a substance according to change in resistance or change in resonant frequency of a CM immunosensor exposed to samples with known and unknown contaminant concentrations.

As shown in FIG. 13, determining the unknown contaminant concentration 1108 includes determining whether ΔR or ΔF of the CM immunosensor exposed to the samples with the known contaminant concentrations more accurately reflects the known contaminant concentrations 1302. Several criteria may be used to make this determination. For example, the ΔR or ΔF of the CM immunosensor of the samples with the known contaminant concentrations that more accurately reflects the known contaminant concentrations may include that which is more proportional to the known contaminant concentrations. In another example, the ΔR or ΔF that more accurately reflects the known contaminant concentrations may include that which is more sensitive to the known contaminant concentrations. If ΔF of the CM immunosensor exposed to the samples with the known contaminant concentrations more accurately reflects the known contaminant concentrations, the unknown contaminant concentration may be determined according to the ΔF of the samples with the known concentrations 1306. If, however, ΔR of the CM immunosensor exposed to the samples with the known contaminant concentrations more accurately reflects the known contaminant concentrations, the unknown contaminant concentration may be determined according to ΔR of the samples with the known concentrations 1308.

If the unknown contaminant concentration is to be determined by the ΔF of the CM immunosensor exposed to the samples with the known contaminant concentrations, the ΔF of the CM immunosensor exposed to the sample with the unknown contaminant concentration is compared with that of the known contamination concentration. The contaminant concentration corresponding to the ΔF of the known contaminant concentration that is closest to the ΔF of the unknown concentration approximately equals the unknown contaminant concentration. A similar process may be used if the unknown contaminant concentration is to be determined by the ΔR.

What is claimed is:

1. A method for determining a concentration of a contaminant in a first sample, the method comprising:
   producing the first sample, comprising adding a plurality of immuno-magnetic beads to a test substance;
   exposing a crystal microbalance (CM) immunosensor to the first sample;
   determining a change in a first motional resistance of the crystal microbalance immunosensor following exposure to the first sample ($\Delta R_1$); and
   determining the concentration of the contaminant in the first sample according to $\Delta R_1$.

2. The method of claim 1, wherein the crystal includes quartz.

3. The method of claim 1 wherein the test substance is a food substance.

4. The method of claim 1, wherein $\Delta R_1$ is measured using a quartz crystal analyzer.

5. The method of claim 1, wherein determining $\Delta R_1$ includes measuring $\Delta R_1$.

6. The method of claim 1, wherein determining $\Delta R_1$ includes measuring a conductance ($G_{f1}$) and a susceptance ($B_{f1}$) of the CM immunosensor exposed to the first sample.

7. The method of claim 6, wherein $G_{f1}$ and $B_{f1}$ are measured approximately simultaneously.

8. The method of claim 6, wherein $\Delta R_1$ is determined as a function of $G_{f1}$ and $B_{f1}$ using a Butterworth-Van Dyke model.

9. The method of claim 1 wherein the contaminant is a *Salmonella typhimurium*.

10. The method of claim 1 wherein the immuno-magnetic beads comprise an antibody specific for a *Salmonella* species.

11. The method of claim 1 wherein the immuno-magnetic beads comprise an antibody specific for *Salmonella typhimurium*.

12. The method of claim 1 wherein the test substance comprises a food sample, a blood sample, or a urine sample.

13. The method of claim 1 wherein the immuno-magnetic beads comprise immuno-magnetic microbeads, or immuno-magnetic nanobeads.

14. The method of claim 1, further comprising:
   adding a plurality of immuno-magnetic beads to a plurality of second samples, wherein each of the second samples comprises a known concentration of the contaminant;
   exposing the CM immunosensor to the plurality of second samples; and
   determining a change in a second motional resistance ($\Delta R_2$) of the CM immunosensor exposed to the plurality of second samples.

15. The method of claim 14, wherein determining $\Delta R_2$ comprises measuring a conductance ($G_{f2}$) and a susceptance ($B_{f2}$) of the CM immunosensor exposed to the plurality of second samples.

16. The method of claim 15, wherein $\Delta R_2$ is determined as a function of $G_{f2}$ and $B_{f2}$ using a Butterworth-Van Dyke model.

17. The method of claim 1 wherein the contaminant is a pathogen, a bacterium, a virus, an insect, or an arachnid.

18. The method of claim 1 wherein producing the first sample further comprises separating the immuno-magnetic beads from the test substance.

19. The method of claim 1 wherein producing the first sample further comprises magnetically separating the immuno-magnetic beads from the test substance.

20. The method of claim 1, wherein the first sample is exposed to the CM immunosensor without separating the immuno-magnetic beads from the test substance.

* * * * *